(12) United States Patent
Wright

(10) Patent No.: US 8,912,373 B2
(45) Date of Patent: Dec. 16, 2014

(54) PROCESS FOR THE DEHYDRATION OF AQUEOUS BIO-DERIVED TERMINAL ALCOHOLS TO TERMINAL ALKENES

(75) Inventor: Michael E. Wright, Ridgecrest, CA (US)

(73) Assignee: The United States of America as Represented by the Secretary of the Navy, Washington, DC (US)

(*) Notice: Subject to any disclaimer, the term of this patent is extended or adjusted under 35 U.S.C. 154(b) by 22 days.

(21) Appl. No.: 13/434,668

(22) Filed: Mar. 29, 2012

(65) Prior Publication Data
US 2012/0238788 A1  Sep. 20, 2012

Related U.S. Application Data

(60) Division of application No. 13/434,474, filed on Mar. 29, 2012, which is a continuation-in-part of application No. 12/511,796, filed on Jul. 29, 2009, now Pat. No. 8,395,007, and a continuation-in-part of application No. 12/550,973, filed on Aug. 31, 2009, now Pat. No. 8,227,651.

(60) Provisional application No. 61/527,943, filed on Aug. 26, 2011.

(51) Int. Cl.

| | |
|---|---|
| *C07C 11/02* | (2006.01) |
| *C07C 11/08* | (2006.01) |
| *C07C 1/20* | (2006.01) |
| *C10G 3/00* | (2006.01) |
| *B01J 37/02* | (2006.01) |
| *B01J 23/00* | (2006.01) |
| *B01J 37/06* | (2006.01) |
| *C07C 1/24* | (2006.01) |
| *B01J 23/06* | (2006.01) |
| *C10G 50/00* | (2006.01) |
| *B01J 21/12* | (2006.01) |
| *C10L 1/08* | (2006.01) |
| *B01J 31/02* | (2006.01) |
| *B01J 37/08* | (2006.01) |

(52) U.S. Cl.
CPC ......... *B01J 23/06* (2013.01); *C10G 2300/1011* (2013.01); *C10G 3/42* (2013.01); *C10G 2300/302* (2013.01); *Y02E 50/13* (2013.01); *B01J 37/0209* (2013.01); *B01J 23/005* (2013.01); *B01J 37/06* (2013.01); *C10G 2300/304* (2013.01); *C10G 2300/307* (2013.01); *C07C 1/24* (2013.01); *C10G 50/00* (2013.01); *C07C 2521/04* (2013.01); *B01J 21/12* (2013.01); *C07C 2523/06* (2013.01); *C07C 2531/12* (2013.01); *C10L 1/08* (2013.01); *B01J 31/0274* (2013.01); *C10G 2400/20* (2013.10); *C10G 3/44* (2013.01); *B01J 37/08* (2013.01)
USPC .............. 585/16; 585/638; 585/639; 585/640

(58) Field of Classification Search
USPC .................................. 585/16, 638, 639, 640
See application file for complete search history.

(56) References Cited

U.S. PATENT DOCUMENTS

| 4,234,752 A | 11/1980 | Wu et al. |
| 4,260,845 A | 4/1981 | Shioyama |

(Continued)

FOREIGN PATENT DOCUMENTS

| EP | 0173471 B1 | 6/1989 |
| WO | WO 2010/055935 A1 | 5/2010 |

(Continued)

OTHER PUBLICATIONS

Williams, et al., "Kineticstudies of catalyticdehydration of tert-butanol on zeolite NaH-ZSM-5"; Journal of Catalysis [online], Jan. 1991,vol. 127, Iss. 1, pp. 377-392.

(Continued)

*Primary Examiner* — Ellen McAvoy
(74) *Attorney, Agent, or Firm* — Charlene A. Haley

(57) ABSTRACT

A method and apparatus for dehydrating bio-1-alcohols to bio-1-alkenes with high selectivity. The bio-1-alkenes are useful in preparing high flashpoint diesel and jet biofuels which are useful to civilian and military applications. Furthermore, the bio-1-alkenes may be converted to biolubricants useful in the transportation sector and other areas requiring high purity/thermally stable lubricants.

17 Claims, 4 Drawing Sheets

(56) References Cited

U.S. PATENT DOCUMENTS

| | | | |
|---|---|---|---|
| 4,473,444 A | 9/1984 | Feldman et al. | |
| 4,772,736 A | 9/1988 | Edwards et al. | |
| 5,158,992 A | 10/1992 | Caselli et al. | |
| 5,830,821 A | 11/1998 | Rohrmann et al. | |
| 6,929,705 B2 | 8/2005 | Myers et al. | |
| 7,235,704 B2 * | 6/2007 | Grund et al. | 585/639 |
| 8,227,651 B1 * | 7/2012 | Harvey et al. | 585/362 |
| 8,242,319 B1 | 8/2012 | Wright et al. | |
| 8,344,196 B2 | 1/2013 | Wright et al. | |
| 8,350,107 B2 | 1/2013 | Wright et al. | |
| 8,373,012 B2 * | 2/2013 | Peters et al. | 585/310 |
| 8,395,007 B2 | 3/2013 | Wright et al. | |
| 8,440,873 B2 * | 5/2013 | Bailey et al. | 585/639 |
| 2001/0006154 A1 | 7/2001 | Krug et al. | |
| 2002/0177728 A1 | 11/2002 | Boudreaux et al. | |
| 2003/0125595 A1 | 7/2003 | Bagheri et al. | |
| 2005/0267271 A1 | 12/2005 | Mink et al. | |
| 2007/0185362 A1 | 8/2007 | Lattner et al. | |
| 2007/0293640 A1 | 12/2007 | Jiang et al. | |
| 2007/0293712 A1 | 12/2007 | Titta et al. | |
| 2008/0102502 A1 | 5/2008 | Foody et al. | |
| 2008/0132730 A1 | 6/2008 | Manzer et al. | |
| 2008/0216391 A1 | 9/2008 | Cortright et al. | |
| 2009/0030239 A1 * | 1/2009 | D'Amore et al. | 568/671 |
| 2009/0124835 A1 | 5/2009 | Yamaguchi et al. | |
| 2009/0139134 A1 | 6/2009 | Yoshikuni et al. | |
| 2009/0299109 A1 | 12/2009 | Gruber et al. | |
| 2009/0305926 A1 | 12/2009 | Wu et al. | |
| 2010/0069589 A1 | 3/2010 | Bradin | |
| 2010/0155333 A1 | 6/2010 | Husain et al. | |
| 2010/0204925 A1 | 8/2010 | Albahri | |
| 2010/0330633 A1 | 12/2010 | Walther et al. | |
| 2011/0061290 A1 | 3/2011 | Aulich et al. | |
| 2011/0111475 A1 | 5/2011 | Kuhry et al. | |
| 2011/0114538 A1 | 5/2011 | Cosyns et al. | |
| 2011/0160502 A1 | 6/2011 | Wu et al. | |
| 2011/0172475 A1 | 7/2011 | Peters et al. | |
| 2012/0207648 A1 | 8/2012 | Wright et al. | |
| 2012/0209036 A1 | 8/2012 | Harvey et al. | |
| 2012/0209039 A1 | 8/2012 | Wright et al. | |
| 2012/0209040 A1 | 8/2012 | Wright et al. | |
| 2012/0209047 A1 | 8/2012 | Wright et al. | |
| 2012/0238788 A1 | 9/2012 | Wright et al. | |
| 2012/0271089 A1 | 10/2012 | Wright et al. | |
| 2013/0197279 A1 | 8/2013 | Wright et al. | |
| 2013/0253236 A1 | 9/2013 | Wright et al. | |

FOREIGN PATENT DOCUMENTS

| | | |
|---|---|---|
| WO | WO 2010/1362989 A2 | 12/2010 |
| WO | 2013032550 | 3/2013 |

OTHER PUBLICATIONS

Leeuwen, et al., "New processes for the selective production of 1-octene"; Coordination Chemistry Reviews [online], Epub, Oct. 16, 2010. vol. 255, Iss. 13-14; pp. 1499-1517.

* cited by examiner

US 8,912,373 B2

PROCESS FOR THE DEHYDRATION OF AQUEOUS BIO-DERIVED TERMINAL ALCOHOLS TO TERMINAL ALKENES

CROSS-REFERENCE TO RELATED APPLICATIONS

This is a divisional application claiming benefit of parent application Ser. No. 61/527,943 filed on Aug. 26, 2011 and Ser. No. 13/434,474 filed on Mar. 29, 2012 which is a continuation-in-part, claiming the benefit of, parent application Ser. No. 12/511,796 filed on Jul. 29, 2009 now U.S. Pat. No. 8,395,007 and Ser. No. 12/550,973 filed on Aug. 31, 2009 now U.S. Pat. No. 8,227,651, whereby the entire disclosure of which is are incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefore.

FIELD OF THE INVENTION

The invention generally relates to conversion of terminal alcohols to the corresponding terminal alkenes with high selectivity and chemical yields. The bio-1-alkenes are useful in the preparation of sustainable and alternative diesel and jet fuels and biolubricants.

BACKGROUND

α-olefins are useful intermediates in preparing diesel and jet/turbine fuels. They are also use in preparing poly-α-olefins (PAOs) and copolymers with ethylene to form low density plastics. If the α-olefins are made from petroleum resources, then there exist several well known processes for ethylene oligomerization that afford α-olefins such as 1-butene, 1-hexene, 1-octene, and so forth, and after a distillation and purification process can yield a single pure terminal olefin. The Shell SHOP process is perhaps the best known to those skilled in the art of ethylene oligomerization.

Obtaining α-olefins made from renewable and sustainable resources requires quite a different approach. Since alcohols can be produced in large scale by fermentation processes, they can be viewed as an attractive feedstock for α-olefins provided that they can be dehydrated in high yield and with high regioselectivity. Particular to α-olefins is a distinct and thermodynamically driven isomerization reaction to the more stable internal-olefin. For example, dehydration of 1-butanol often produces a mixture of 1-butene and 2-butene where the latter is a result of 1-butene isomerizing to the more thermodynamically stable 2-butene. It is well known this type of double-bond isomerization is facilitated by acid catalysts; hence, to maintain 1-butene as the dominant product, a successful process must avoid interaction with acidic catalyst sites.

Bio-1-butanol in particular has a rich history of success and large scale commercial production since the discovery by Louis Pasteur in 1862 where he first revealed bacteria that could ferment sugars to a mixture of acetone, 1-butanol, and ethanol (ABE). Since Pasteur's initial discovery of the ABE process many advances have been made in the fermentation process to optimize bio-1-butanol production and reduce ethanol and acetone co-production. Most notably are the successful efforts using non-engineered bacteria that in fact have led to commercial plants operating for decades that produce bio-1-butanol.

Since fermentations are carried out in water, separation of the fermentation products from the water and bacteria "soup" is energy and time intensive. In the case of bio-1-butanol, several methods have been reported for isolating the alcohol component. One method that has found commercial success is use of a sparging gas (e.g. carbon dioxide or steam) that carries the more volatile bio-1-butanol/water azeotrope away from the fermentation broth. Other more academic approaches involve pervaporization. In this case, a selective-membrane material is used that permits bio-1-butanol pass through, thus leaving the bacteria and water behind. Regardless of the method it is evident to those skilled in the art that removing the last traces of impurities and water are costly in energy and time. The methods vary significantly in capabilities. However, water and impurities are a direct and unavoidable consequence from bioalcohol fermentation processing. Ruwet et al. (Bull. Soc. Chim. 1987, 96, 281-292) discuss the problems in using a wet ABE bio-1-butanol feed in a dehydration reaction to afford a mixture of olefins. More recently, D'amore et al. (patent appl. US 2008/0015395 A1) showed extreme difficulty in dehydrating aqueous solutions of 1-butanol using a variety of acid catalysts to afford a mixture of olefins and other oxygenated products (e.g. ethers) coupled to high amounts of unreacted 1-butanol. There is clearly no obvious and proficient method for preparing terminal bio-1-olefins efficiently from bio-1-alcohols that contain water as a major impurity.

SUMMARY

Embodiments of the invention generally relates to bio-1-alcohol dehydration catalyst including, at least one inorganic solid support, a basic aqueous solution, where the inorganic solid support is subjected to a first treatment with the basic aqueous solution, at least one first inert gas or air, where the base treated inorganic solid support is dried under a heated stream of the air or inert gas, where the first base treated inorganic solid support is treated with at least one organosilane diluted in at least one hydrocarbon solvent, and at least one second inert gas or air, where the second treated inorganic solid support is heated and dried under the second air or an inert gas. In embodiments, the solid support is γ-alumina. In other embodiments, the solid support is zinc aluminate ($ZnAl_2O_4$).

In embodiments, the solid support is prepared by heating an equal molar ratio of zinc oxide and γ-alumina at temperatures of 800° C. to 1100° C. In other embodiments, the solid support is prepared by heating a mixture of zinc oxide and γ-alumina at temperatures of 800° C. to 1100° C., where the zinc oxide is utilized is in the amount of 1 to about 20 mol-% excess. In embodiments, the catalyst is treated with an aqueous base solution that is comprised of 1-20 wt-% sodium or potassium hydroxide for a period of 1 to about 12 hours.

In embodiments, the catalyst is treated with an aqueous base solution and then dried at 100-150° C. for about 4 to about 24 hours under an atmosphere of the first air or the first inert gas being nitrogen. In embodiments, the organosilane selected from the group consisting of $R_3SiCl$, $R_2SiCl_2$, and $RSiCl_3$, wherein R is a linear or branched alkyl chain of 1 to 20 carbons. In other embodiments, the organosilane selected from the group consisting of $R_3SiCl$, $R_2SiCl_2$, and $RSiCl_3$, wherein R is a combination of linear or branched alkyl chain of 1 to 20 carbons and at least one phenyl ring. In yet other embodiments, the organosilane selected from the group consisting of R₃SiCl, R₂SiCl₂, and RSiCl₃, wherein R is an aromatic substituent. Another aspect of the invention includes methods for making bio-alkenes utilizing the catalyst manufacture thereabove.

Embodiments of the invention give instant access to a catalyst system and process that can take in a feed of terminal bioalcohol including from 0.1 or about 0.1 to about 90 wt-% water and produce the respective α-olefin with 92-99% regiochemical selectivity and in a single pass over the catalyst system afford a chemical conversion of greater than 95%. At least one solid phase catalyst is maintained at a temperature of 200° C. to 400° C., with fed of bioalcohol at a pressure of 1 to 1000 psig to produce at least one bio-1-alkene in high selectivity. In one embodiment, bioalcohol is obtained from a fermentation broth after removal of minor acidic contaminants.

Embodiments of the invention generally relate to alternative fuels and the making of bio-1-alkenes that can be utilized to prepare drop-in and full performance diesel biofuel, jet biofuel, and biolubricants.

Figure 1:
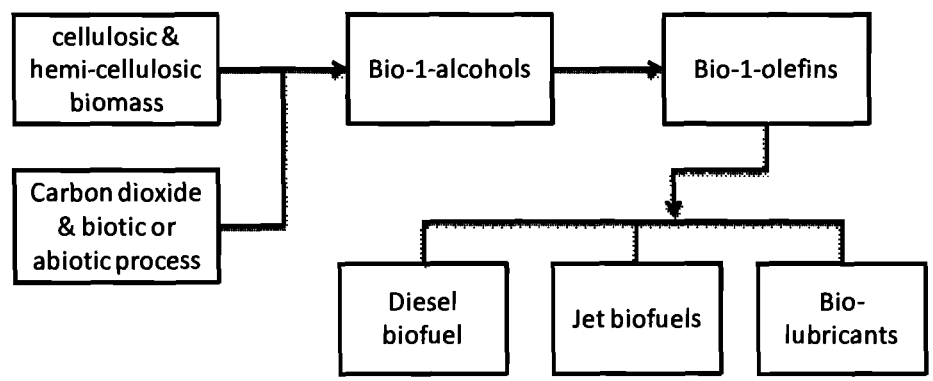
FIG. 1 illustrates a general overview for creating renewable and sustainable biodiesel, biojet, and biolubricants based on a feed stream of bio-1-alcohols, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION

Embodiments of this invention are to place at least one bio-1-alcohol including water in contact with a solid phase catalyst to produce and isolate at least one bio-1-olefin with high selectivity (>92%):

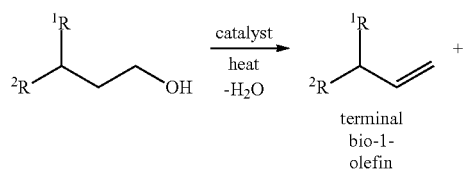

terminal bio-1-olefin

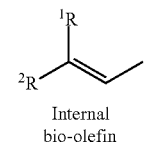

Internal bio-olefin

The water in the bio-1-alcohol mixture can be from 0.1 to 90 wt-% or 1 to 20 wt-% or 17 wt-%. ¹R and ²R can be hydrogen, an alkyl radical of C1 to C20, and any combination thereof.

An aspect of the invention relates to a method for dehydrating bio-1-alcohol including; providing at least one bio-1-alcohol, where the bio-1-alcohol having from 1 ppm to 90% water, subjecting and heating the bio-1-alcohol with at least one desired catalyst, and controlling dwell time and temperature with at least one purge gas at a rate of about 0.01 to about 1.0 per mass of said catalyst/hour to produce bio-1-alkene with high selectivity (>95%). Another aspect of the invention relates to a bio-1-alkene product including; at least one bio-1-alcohol, at least one desired catalyst, where the bio-1-alcohol is subjected and heated to at least one desired catalyst, and at least one purge gas which controls dwell time and temperature at a rate of about 0.01 to about 1.0 per mass of said catalyst/hour to produce bio-1-alkene product.

Embodiments of the invention including bio-1-alcohol it is bio-1-butanol. In embodiments including bio-1-alkene it is bio-1-butene. In embodiments, the catalyst is a equal molar combination of zinc oxide and alumina that has been treated at a temperature of 800 to 1000° C. for periods of 24 to 48 h prior, then treated with base, washed, air dried, and then treated with 0.1-20 wt-% of a chlorosilane in a hydrocarbon solvent. In embodiments, at least one chlorosilane is taken from the group consisting of triphenylchlorosilane, diphenyldichlorosilane, phenyltrichlorosilane. In other embodiments, the chlorosilane is at least one trialkylchlorosilane which is taken from the group consisting of dialkyldichlorosilane, alkyltrichlorosilane. In embodiments, the alkyl is selected from the group consisting of methyl, ethyl, propyl, butyl, iso-butyl, and up to C20 alkyl chains as a pure linear or branched or a mixture thereof.

In embodiments, the catalyst is an alumina-based catalyst that has been treated with an aqueous base solution, washed with water, dried, reacted with at least one chlorosilane in the amount of 0.1-20 wt-%, washed with a hydrocarbon solvent, and air dried. In other embodiments, the base is selected from sodium or potassium hydroxide at concentrations in water of 1 to 20 wt-% wherein 5 wt-% and contact time with the γ-alumina is from 1-8 h or 2 h. In other embodiments, the catalyst is ZnAl₂O₄. In yet other embodiments, the catalyst is a γ-alumina catalyst that has been modified by reaction with base and then modified with an organosilane. In these embodiments, at least one chlorosilane is taken from the group consisting of triphenylchlorosilane, diphenyldichlorosilane, or phenyltrichlorosilane. In these embodiments, at least one chlorosilane is taken from the group consisting of trialkylchlorosilane, dialkyldichlorosilane, or alkyltrichlorosilane. In these embodiments, the alkyl is selected from the group consisting of methyl, ethyl, propyl, butyl, iso-butyl, and up to C20 alkyl chains as a pure linear or branched or a mixture thereof.

In embodiments, the purge gas is nitrogen, argon, or a mixture of the two gases. In embodiments, the ZnAl₂O₄ is obtained by recycling of spent catalyst through heating first to 800-1100° C., with 900-1000° C. for a period of 4 to 24 h or 16 h of heating, all in the presence of nitrogen or air. In embodiments, the heating ranges for the dehydration range from about 300° C. to about 420° C. or about 360 to about 385° C.

In embodiments, the catalyst is a combination of zinc oxide and alumina not in a one to one mole ratio. In embodiments, the catalyst is an alumina-based catalyst specifically washed with base solutions. In other embodiments, the catalyst is an alumina-based catalyst modified with an organosilane. In alternative embodiments, there is no purge gas. In other embodiments, the purge gas is nitrogen and/or argon. In embodiments, the heating step ranges from temperatures of about 300° C. to 420° C. In embodiments, the bio-1-alcohol is 1-pentanol and/or 1-hexanol. In other embodiments, the bio-1-alcohol comprises long chain bioalcohols including 1-hexadecanol.

Embodiments of the invention include at least one bio-1-alkene being contacted with a Ziegler-Natta catalyst to form oligomers useful in preparing high flashpoint biodiesel fuels, which includes flashpoints in the range of 61 to 100 deg ° C. and Cetane rating of 45 to 60. In other embodiments, at least one bio-1-alkene is contacted with a Ziegler-Natta catalyst to form oligomers useful in preparing high flashpoint biojet fuels, these include flashpoints from 61 to 100° C. and cold flow viscosities of <8.5 cSt at −20° C. in embodiments, at least one bio-1-alkene is contacted with a Ziegler-Natta catalyst to form oligomers useful in preparing biolubricants with viscosities in the range of 1 to 10,000 cSt at 25° C. In embodiments, the fuels are a bio-alkene fuel precursor produced by the methods disclosed. A bio-alkene produced by the method described above.

For an embodiment in this invention the bio-1-alcohol can include water at levels as low as 1 to 1000 ppm where equal performance of catalyst to afford bio-1alkene is seen throughout the entire range of low water content and maintains high selectivity for extended periods of time on stream, typically 6-12 months.

Possible alternatives would be silica and alumina solid phase catalysts as well as standard mineral acid catalysts. These all give complicated mixtures of products. There are patents in the 1980's that describe the catalytic dehydration of terminal alcohols over solid phase catalysts, however the process described does not relate to bio-1-alcohols and does not handle the impurities (e.g. water) commonly found in bio-1-alcohols produced by fermentation processes and potentially other biotic procedures. The art had water contained in the alcohol feed which would deactivate the catalyst. Since water is a common co-product in making bioalcohols, there exists a significant limitation in the art. Work in 2005 specifically pointed out the shortcomings of using γ-alumina to dehydrate 1-alcohols. The study (Makgoba et al. *Applied Catalysis A: General* 2005, 297(2), 145-150) showed γ-alumina showed significant loss in selectivity for conversion of 1-alcohols to 1-alkenes (α-olefins) with time on stream (TOS) leading to production of internal olefins although conversion rate of alcohol to alkenes remained steady.

Currently dehydration methods form a mixture of alkenes, some being internal-alkenes. The latter are far less effective in certain types of Zeigler-Natta polymerization chemistry that are of particular interest in preparing high flashpoint diesel and jet fuels and for making biolubricants. Thus for utilizing a bio-1-alcohol (e.g. bio-1-butanol) as feedstock, it is highly desirable to have a selective dehydration process that affords rapid and high conversion to the terminal-olefin (e.g. bio-1-butene) and is accompanied by no carbon skeletal rearrangement (e.g. to iso-butylene). In embodiments of the invention, bio-1-butene can be utilized to make drop-in diesel and jet biofuels as well as biolubricants in an energy manner [FIG. 1]. Thus, embodiments of the invention give instant access to the conversion of bio-1-butanol including small to large amounts of water, to bio-1-butene with high selectivity and chemical conversion. The bio-1-butene in turn is useful in preparing products that are environmentally beneficial and reduce green house gases compared to petroleum equivalents.

Current methods for dehydrating alcohol leads to a variety of regiosiomers. For example, 1-butanol if dehydrated by typical solid phase catalysts, like γ-alumina, affords a mixture of 1-butene (~70%) and 2-butene (~30%). Other examples, like the dehydration of iso-butyl alcohol (Taylor et al. *Topics Catal* 2010, 53, pp 1224-1230), afford regio-isomers as well as skeletal rearrangements (e.g. to 2-butene). Embodiments of this invention describe a catalyst system and approach that lead to high regiochemical dehydration of 1-bioalcohols including water and retain selectivity with extended time on stream (TOS). Hence, dehydration of bio-1-butanol using embodiments of the invention of the process described herein leads to bio-1-butene in better than 95% chemical yield and 92-99% selectivity for bio-1-butene with at least one catalyst charge can be used continuously for 1-12 months and show no decrease in selectivity for the terminal bio-1-olefin.

Other organic contaminants including esters and ketones, but not limited to, can be tolerated at various levels depending upon the bio-1-alcohol feedstock used. Ranges from 0.0 to 5 wt-% can be tolerated, or 0.0 to 0.5 wt-% the level of organic contaminants.

Figure 2:
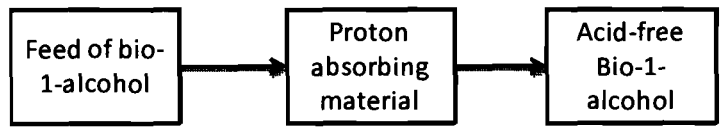
FIG. 2 illustrates a process for producing a bio-1-alcohol free of acidic components and used as a feed stream, according to embodiments of the invention.

In the case of acidic-contaminants, it is best practice to remove them by pretreatment of the bioalcohol mixture either in solution or gas phase [FIG. 2]. This can be accomplished by contacting the bioalcohol mixture with a water solution including an organic or inorganic base. Typical examples would be aqueous sodium bicarbonate or similar inorganic bases dissolved in water. A solid phase reagent capable of absorbing protons can be utilized. Examples of a solid support capable of removing acidic organics would include poly (vinylpyridine) or related porous polymer-bound organic bases known to those skilled in the art of functionalized organic polymers. Time on stream for catalysts including impurities greater than disclosed in embodiments of the invention can lead to a shorter catalyst lifetimes. However, catalysts can be reactivated by heating to 1000° C. for a period of 4-24 h and then modified for embodiments of the invention using a similar modification protocol as described for a new γ-alumina.

Figure 3:
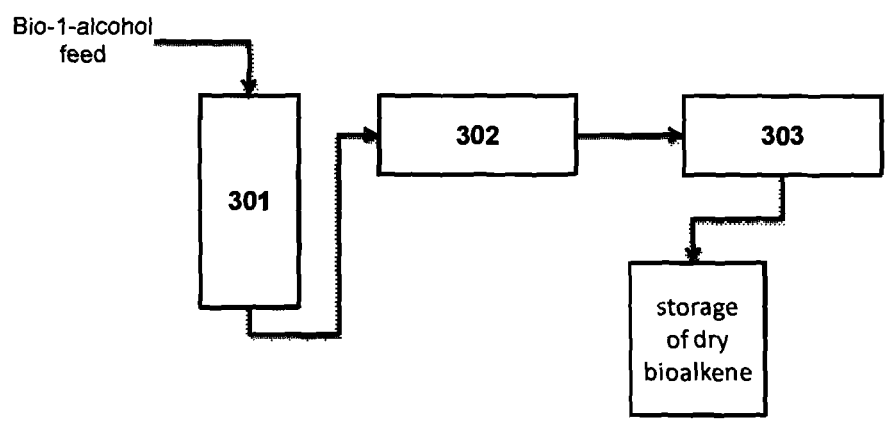
FIG. 3 illustrates a process for making bio-1-olefins, according to embodiments of the invention.

A feedstock of bio-1-alcohol is passed through a heated vessel 301 including the dehydration catalyst [FIG. 3]. A purge gas is used to control dwell time in the reactor chamber and the temperature is modified to optimize bio-1-alkene production for a particular bioalcohol feedstock. Rates of bio-1-alcohol feedstock can be from 0.01 to 1.0 mass per mass of catalyst/h and can fall outside this region. Water content in the bio-1-alchohol feedstock can be from 1 ppm to 90 wt-%, with 1 to 20 wt-% for optimum production of bio-1-alkene, however, other levels of water content can be used in embodiments of the invention.

Catalysts used in 301 for embodiments of the invention may left as powders in the range of 10-1000 micron, or 50-200 micron, or they can be pelletized using techniques common to those skilled in the art. The advantage of creating pellets is a decrease in vessel back pressure. This may be important where physical process requirements require long reaction tubes and/or where low head-pressures are desirable. Pellets may be any shape or size; however, a range is from ⅛" diameter to ¼" diameter with lengths 1 to times the diameter, but not limited to.

Water is separated from the bioalkene product stream by fractionation through a distillation column 302. Physical separation of layers can be used when the bioalkene product is sufficiently high boiling, typically above 30° C., then 302 would function as a decanter rather than distillation column. The bioalkene product will always be the top layer and it will be siphoned from the top of the vessel with the separated water continuously drained from 302.

Final removal of final traces of water and oxygenated organics can be done by passing the bioalkene stream through a fixed bed of activated alumina, molecular sieves, Celite, activated charcoal, size-exclusion type of media, or a combination thereof included in vessel 303. Reactivation of the fixed-bed materials is possible by heating under a purge of hydrocarbon or inert gas while heating to temperature of 50 to 200° C. or 100° C. Vessel 302 could also be a series of membranes and/or bed of ionic-liquids that are well known for permitting selective passage of non-polar molecules and retaining more polar organics (e.g. ethers and alcohols).

Example 1

Two runs were carried out according to the process of embodiments of the invention for the dehydration of bio-1-butanol including 18% water by weight. The catalyst for the runs was prepared from γ-alumina powder (300 g, ~185 m$^2$/g, pore volume 0.43 cc/g) obtained from Strem Chemical and was modified with base wash, dried, and then modified by treatment with 2 wt-% of diphenylsilane dichlorosilane in hexanes. The modified alumina (~280 g) was air dried and loaded into the fix-bed continuous flow reactor and heated to 380° C. All runs were performed with a feed of 0.8 mL/min at a pressure of 30 psig created with flow restriction to maintain adequate flow stability with the HPLC pump. Table I presents the total chemical yield of biobutenes, regioselectivity for bio-1-butene, and time on stream (TOS) for the catalyst.

TABLE I

| Run | Chemical Yield of Biobutenes (%) | Regioselectivity for bio-1-butene (%) | Time on Stream for Catalyst (days) |
|---|---|---|---|
| 1 | 96 | 94 | 3 |
| 2 | 98 | 95 | 20 |
| 3 | 96 | 94 | 123 |

Figure 4:
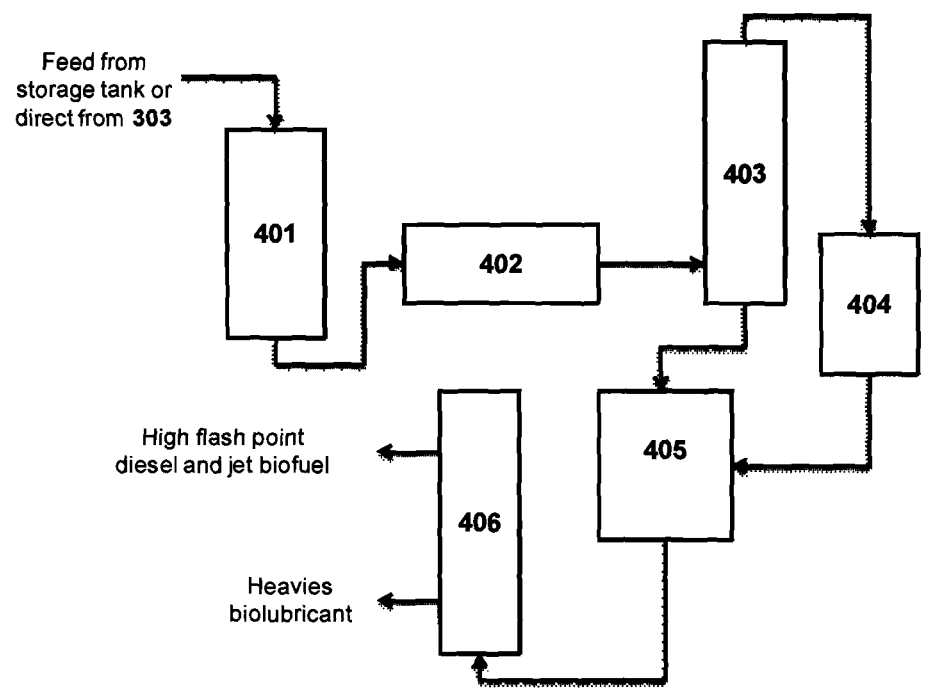
FIG. 4 illustrates a process for converting a bioolefin mixture that is highly enriched in bio-1-olefin to diesel and jet biofuels and biolubricants, according to embodiments of the invention.
Figure 5:
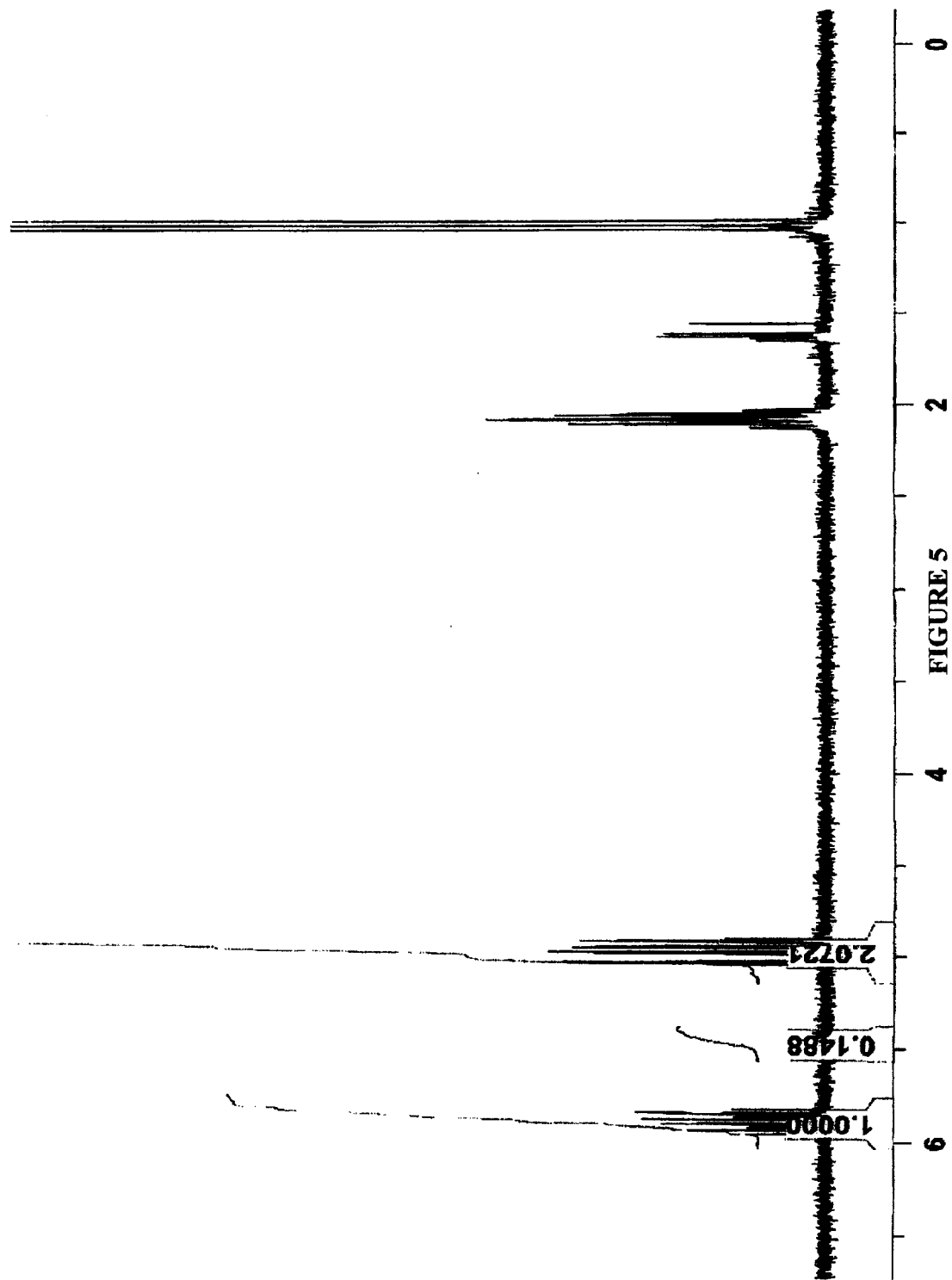
FIG. 5 shows a proton nuclear magnetic resonance (NMR) spectrum of biobutenes produced as a result of contacting bio-1-butanol (15 wt-% water content) with a silane-modified γ-alumina dehydration catalyst, according to embodiments of the invention.

The final bioalkene product may be used immediately in the process to make diesel and jet biofuels and/or biolubricants [FIG. 4]. Alternatively, the bioalkene product may be stored for periods of 1 h to 6 months, or 1-8 h of time.

Products from embodiments of the invention can be placed in contact with a Ziegler-Natta catalyst (401) and rapidly converted to α-olefin oligomers. The reactor type used in step 401 can be a continuous flow or simple batch. Step 401 can also utilize an isomerization catalyst to fully utilize internal olefins that might be present in minor amounts. The catalysts are removed from the α-olefin oligomers mixture and the lights are removed in 403 and then subjected to a highly energy and chemically efficient dimerization reaction (404), thus doubling their molecular weight so they effectively fit into a useful range of boiling point and viscosity for use as a diesel, jet, and/or biolubricant. The bottoms from 403 are combined with product from 404 (after catalyst removal) and subjected to hydrogenation in 405 and followed by a finishing process (i.e. fractionation) that affords high flash point (61-100° C.) diesel and jet fuels as well as biolubricants with exceptional thermal stability.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A bio-1-alkene product prepared by the process, comprising:
   at least one bio-1-alcohol; and
   at least one base treated protected catalyst at elevated temperatures
   to produce bio-1-alkene product having a terminal 1-olefin selectivity of about 92% to 99%.

2. The product by process according to claim 1, wherein said bio-1-alcohol is bio-1-butanol.

3. The product by process according to claim 1, wherein said bio-1-alkene fuel is bio-1-butene.

4. The product by process according to claim 1, wherein said catalyst is a combination of zinc oxide and alumina not in a one to one mole ratio.

5. The product by process according to claim 1, wherein said catalyst is an alumina-based catalyst specifically washed with base solutions.

6. The product by process according to claim 1, wherein said catalyst is an alumina-based catalyst modified with an organosilane.

7. The product by process according to claim 1, wherein said catalyst is $ZnAl_2O_4$.

8. The product by process according to claim 1, further comprising at least one purge gas being-nitrogen and/or argon.

9. The product by process according to claim 1, wherein said heating step ranges from temperatures of about 200° C. to 420° C.

10. The product by process according to claim 1, wherein said bio-1-alcohol is 1-pentanol and/or 1-hexanol, renewable alcohols of general formula HO(CH2)n(CH3)m with n>/= to 2 and n+m ranging from 3-20, or renewable alcohols of general formula HO(CH2)n(CH3) with n being any integer from 2 to 19.

11. The product by process according to claim 1, wherein said bio-1-alcohol comprises long chain bioalcohols including 1-hexadecanol.

12. The product by process according to claim 1, wherein said at least one bio-1-alkene is contacted with a Ziegler-Natta catalyst to form oligomers useful in preparing high flashpoint biodiesel fuels, which includes flashpoints in the range of 61 to 100 deg ° C. and Cetane rating of 45 to 60.

13. The product by process according to claim 1, wherein said at least one bio-1-alkene is contacted with a Ziegler-Natta catalyst to form oligomers useful in preparing high flashpoint biojet fuels, these include flashpoints from 61 to 100° C. and cold flow viscosities of <8.5 cSt at −20° C.

14. The product by process according to claim 1, wherein said at least one bio-1-alkene is contacted with a Ziegler-Natta catalyst to form oligomers useful in preparing biolubricants with viscosities in the range of 1 to 10,000 cSt at 25° C.

15. A bio-alkene fuel precursor produced by the method of claim 1.

16. A bio-alkene produced by the method of claim 1.

17. The product by process according to claim 1, further comprising at least one purge gas which controls dwell time and temperature at a rate of about 0.01 to about 1.0 per mass of said catalyst/hour.

* * * * *